United States Patent [19]

Tanaka

[11] Patent Number: 5,707,342
[45] Date of Patent: Jan. 13, 1998

[54] PROTECTOR GIRDLE FOR ENDOSCOPIC INSERTION INSTRUMENT

[75] Inventor: Toshizumi Tanaka, Omiya, Japan

[73] Assignee: Fuji Photo Optical Co., Ltd., Omiya, Japan

[21] Appl. No.: 754,370

[22] Filed: Nov. 22, 1996

[30] Foreign Application Priority Data

Nov. 24, 1995 [JP] Japan ..................... 7-327894

[51] Int. Cl.⁶ .................................................. A61B 1/04
[52] U.S. Cl. .................................... 600/114; 600/121
[58] Field of Search .......................... 600/101, 104, 600/114, 115, 116, 119, 121, 129, 134, 139, 186, 203; 606/198; 604/96, 105, 106, 107, 108, 109

[56] References Cited

U.S. PATENT DOCUMENTS

| | | | |
|---|---|---|---|
| 4,207,872 | 6/1980 | Meiri et al. | 600/115 X |
| 4,608,965 | 9/1986 | Anspach, Jr. et al. | 600/204 X |
| 5,112,347 | 5/1992 | Taheri | 604/106 X |
| 5,203,773 | 4/1993 | Green | 604/105 X |
| 5,345,927 | 9/1994 | Bonutti | 600/204 X |

*Primary Examiner*—Beverly M. Flanagan
*Attorney, Agent, or Firm*—Oblon, Spivak, McClelland, Maier & Neustadt, P.C.

[57] ABSTRACT

A protector girdle to be wrapped around an endoscopic insertion instrument prior to introduction into a body cavity through a cannula of a trocar for protecting a soft skin layer on a flexible section of the insertion instrument from sharp edges at the fore end of the cannula. The protector girdle is formed of a generally rectangular sheet of rigid and slippery material with a restorative spring force, and provided with an adhesive band zone defined in a predetermined width along one side of the rectangular sheet, and a large number of elongated flap cover strips cut in the remainder of the sheet material in a predetermined pitch along the adhesive band zone and having free ends on the other side of the sheet remote from the adhesive band zone. When the protector girdle is fitted on an endoscopic insertion instrument, a soft skin layer in a flexible section is securely protected by the respective flap cover strips while passage through sharp edges at the fore end of a cannula.

8 Claims, 7 Drawing Sheets

PROTECTOR GIRDLE FOR ENDOSCOPIC INSERTION INSTRUMENT

BACKGROUND OF THE INVENTION

1. Field of the Art

This invention relates to a protector girdle for use with an endoscopic insertion instrument to be introduced into a body cavity by way of a cannula of a trocar or with a similarly rod-like insertion instrument for protection of a soft skin layer in a flexible section of the insertion instrument.

2. Prior Art

Taking endoscopes as a typical example of tubular insertion instruments designed to be introduced into body cavities, there are canal type endoscopes which utilize a naturally open canal as a path of insertion like peroral endoscopes, and percutaneous type endoscopes to be inserted through a punctured hole like laparoscope and arthroscope. For instance, in the case of a laparoscope, its insertion instrument is introduced into an abdominal cavity through a path of insertion which is punctured through skin layers. Besides intraperitoneal examinations, laparoscope are increasingly used in the so-called keyhole operations on the lever or other organs, puncturing a plural number of small holes as insertion paths to an abdominal cavity for a laparoscope and forceps or other necessary operation instruments and, manipulating these instruments through the small punctured holes, instead of conventional peritoneotomy, in view of less damages to the patient and quicker recovery after an operation.

Normally, for a laparoscope, a path of insertion into a body cavity of interest is secured by the use of a trocar either of a type which is designed simply as a puncturing means for opening a hole in abdominal walls for the introduction of the laparoscope or of a type which is designed to penetrate through abdominal walls along with a cannula which serves as a guide pipe for introducing a laparoscope into an abdominal cavity. In the latter case, a trocar is assembled into a fore end portion of a cannula which is in the form of a rigid pipe with an inner diameter suitable for receiving a laparoscope. The trocar is removably contained in a fore end portion of the rigid cannula in such a way that a sharp-pointed end of the trocar is projected from the fore end of the cannula. The cannula is thinned down at its fore end to present a streamlined profile free of stepped surfaces when assembled with the trocar. After insertion into an abdominal cavity in an assembled state, the trocar is extracted out of the cannula and instead an insertion instrument of a laparoscope is introduced into the body cavity through the cannula, for example, for an intracelial examination.

The rod-like insertion instrument of the laparoscope, which is received in the rigid body of the cannula is also in a rigid form except for a flexible angle section extending over a certain length between a rigid pipe section of the insertion instrument and a distal end section which contains illumination and observation windows for the laparoscope. More specifically, the insertion instrument of the laparoscope is composed of, successively from its base end, a rigid pipe section, a flexible angle section and a tip end section, and at least the angle section and the tip end section need to be protruded into a body cavity from the fore end of a cannula. The direction of view field of the laparoscope can be changed arbitrarily by bending the angle section through a control means which is provided on a gripping head of the laparoscope.

In this connection, prior to introduction of the laparoscopic insertion instrument, in many cases an abdominal cavity is inflated with a pneumoperitoneum gas for the purpose of preventing intracavitary walls getting injured by contact with the insertion instrument when the latter is being moved, for example, for the purpose of relocating the distal end section in a particular region of the abdominal cavity or for the purpose of securing a necessary space within the abdominal cavity for turning the observation window at the distal end of the insertion instrument into desired directions. In order to keep the abdominal cavity in the inflated state during an examination, the insertion instrument is dimensioned to fit in the cannula substantially hermetically to prevent leakage of the pneumoperitoneum gas through the cannula, by reducing to a minimum a dimensional difference between the inside diameter of the cannula and the outside diameter of the insertion instrument.

As mentioned hereinbefore, the fore end of the cannula is thinned down in the fashion of sharp edges of a knife blade, so that there are always possibilities of an outer skin layer of soft synthetic resin material on the angle section being scraped off when slid against the sharp edges at the fore end of the cannula. Especially, if the angle section is in a bent state when withdrawn into the cannula, for example, on extracting the laparoscopic insertion instrument, it is very likely for the soft outer skin layer to be scraped off and damaged to a material degree, leaving debris of scraped outer skin layer within the patient body.

Various attempts have thus far been made to solve this problem, for example, as described in U.S. Pat. No. 4,972, 827 which, as a protection means for endoscopic insertion instrument, employs a guide pipe to be interposed between a cannula of a trocar and an endoscopic insertion instrument. This prior art guide pipe is so dimensioned as to have an outside diameter slightly smaller than the inside diameter of the cannula and an inside diameter slightly larger than the outside diameter of the endoscopic insertion instrument. The guide pipe is rounded off at its fore end, which is projected forward of the sharp fore edges of the cannula when assembled into the latter for use.

By the interposition of the guide pipe as described above, it becomes possible to preclude possibilities of the outer skin layer of the angle section on the endoscopic insertion instrument from being scraped off or materially damaged by sliding contact with sharp edges at the inner end of the cannula even if the angle section is withdrawn in a bent state. However, this prior art guide pipe still has problems of its own. More specifically, the guide pipe needs to be formed of a rigid material with a substantial thickness for its protective functions. Therefore, it becomes necessary to use a cannula of a larger size in inside diameter to receive the guide pipe along with the insertion instrument of an endoscope, and to puncture a greater hole in abdominal walls. Besides, the guide pipe has to be retained in a protruded position by means of a mechanism which holds the guide pipe fixedly in a desired position relative to the cannula despite complication in construction.

SUMMARY OF THE INVENTION

Under the circumstances as explained above, it is an object of the present invention to provide an extremely simple protection means which can securely prevent damages to a soft skin layer on a flexible section of an insertion instrument to be introduced into a body cavity through a cannula as in the case of a laparoscopic insertion instrument or the like.

It is a more specific object of the present invention to provide a protector girdle of an extremely simple construction, for fitting on a laparoscopic insertion instrument or the like to protect a soft skin layer of the insertion instrument as it is withdrawn tightly into a cannula in contact with sharp edges at the fore end of the cannula.

In accordance with the present invention, the above-mentioned objectives are achieved by the provision of a protector girdle to be wrapped around an endoscopic insertion instrument prior to introduction into a body cavity through a cannula of a trocar for protecting a soft skin layer on a flexible section of the insertion instrument from sharp edges at the fore end of the cannula, the protector girdle including a generally rectangular sheet of rigid and slippery material with a restorative spring force, an adhesive band zone defined in a predetermined width along one side of the rectangular sheet, and a large number of elongated flap cover strips cut in the remainder of the sheet material in a predetermined pitch along the adhesive band zone and having free ends on the other side of the sheet remote from the adhesive band zone, the protector girdle being fitted on the endoscopic insertion instrument by bonding the adhesive band zone around a proximal end portion of the flexible section of the insertion instrument in such a manner as to cover the soft skin layer under the respective flap cover strips.

In this instance, the respective flap cover strips are preferred to be rounded off at corner edges of the respective free ends to remove sharp points or edges which might be hazardous to intracavitary walls. Besides, in order to hold the protector girdle stably in position on the insertion instrument and to ensure smooth passage of the girdled flexible section through the fore end of a cannula, it is desirable to wrap an adhesive anchor tape on and around marginal edges of the adhesive band zone on the proximal side of the protector girdle.

If desired, the protector girder may be provided in the form of an elongated continuous girder sheet which contains a large number of protector girdle units in a continuously connected form and which can be cut into unit lengths each containing an adhesive band zone and a plural number of protective flap cover strips over a length suitable for covering a flexible section of an endoscopic insertion instrument. In such a case, a separator sheet is releasably bonded on adhesive sides of the adhesive band zone on the continuous girdle sheet and of the anchor tape to keep them in unexposed state while in storage and at the same time to prevent them from sticking to each other. Preferably, the continuous girdle sheet is provided slits across the adhesive band zone at predetermined intervals along the length thereof, so that one can separate individual protector girdle units easily without using scissors.

BRIEF DESCRIPTION OF THE DRAWINGS

The above and other objects, features and effects of the invention will become apparent from the following particular description of the invention, taken in conjunction with the accompanying drawings which show by way of example preferred embodiments of the invention and in which.

DESCRIPTION OF PREFERRED EMBODIMENTS

Figure 1:
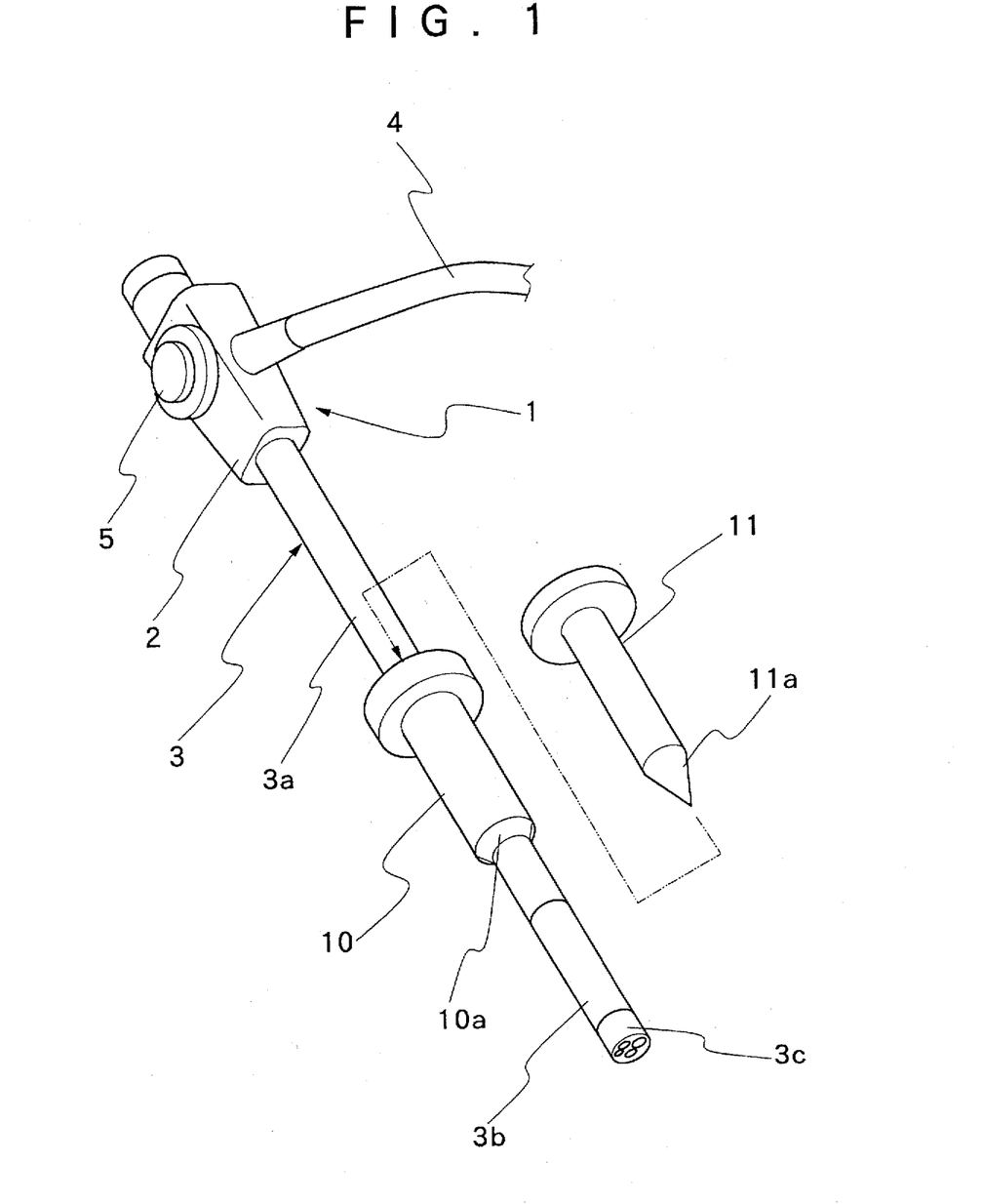
FIG. 1 schematically shows a laparoscope as a typical example of endoscopic insertion instrument, along with a cannula of a trocar which serves as a guide means in introducing the laparoscope into a body cavity.

Hereafter, the invention is described more particularly by way of its preferred embodiments with reference to the accompanying drawings. Referring first to FIG. 1, there shown a laparoscope, representing an endoscopic insertion instrument, and a cannula of a trocar to be used as guide means in introducing the laparoscope into a body cavity. In this figure, indicated at 1 is an endoscope 1 which is largely constituted by a manipulating head 2, an insertion instrument 3 extended from the manipulating head 2 on the front side thereof, and a flexible light guide cable 4 which is led out on the rear side of the manipulating head 2. The endoscopic insertion instrument 3 is provided with a rigid section 3a in the form of a rigid pipe extending over a predetermined length from a proximal end of the insertion element which is connected to the manipulating head 2. Connected successively to the fore end of the rigid section 3a are a flexible angle section 3b and a distal end section 3c which contains endoscopic observation means such as illumination and observation windows. The angle section 3b can be flexed to turn the tip end section 3c into directions of particular interest.

Indicated at 10 is a cannula in the form of a rigid pipe which is designed to receive a trocar 11. The trocar 11 is sharp-pointed at its fore end 11a and provided with a shank 11b of a diameter which is slightly smaller than the inside diameter of the cannula 10. The fore end of the cannula 10 is thinned down into a blade-like sharp edges 10a to present a smooth streamlined profile substantially free of stepped surfaces when assembled with the trocar 11. For introduction into an abdominal cavity, for example, the trocar 11 which is assembled into the cannula 10 is driven to pierce directly through abdominal walls, and then extracted out of the cannula 10, which serves as a guide passage into the abdominal cavity for the insertion instrument 3 of the endoscope 1 to be introduced thereinto.

Of the endoscopic insertion instrument 3 which is guided through the cannula 10, the rigid section 3a is constituted by a rigid pipe of a length greater than that of the cannula 10. The flexible angle section 3b, which is connected to the fore end of the rigid section 3a, can be bent to turn the distal end section 3c into a desired direction by manually rotating an angle knob 5 which is provided on the manipulating head 2. For this purpose, the angle section 3b is internally provided with flexible joints which are constituted by a series of pivotally connected angle rings. The adjacent angle rings are connected by pivotal joints which are located either at lateral sides or alternately at lateral sides and top and bottom sides thereof. The pivotal joints at the lateral sides permit upward and downward flexing movements while the pivotal joints at the top and bottom sides permit rightward and leftward flexing movements of the angle section 3b. Combinations of lateral pivotal joints with top and bottom pivotal joints permit to bend the angle section 3b in upward and downward directions as well as in leftward and rightward directions to turn the tip end section 3c into arbitrary directions. The angle rings are wrapped in a netting layer of metal wire or the like, and then in urethane resin or the like which is laminated on the netting layer to form a soft skin layer on the outer side of the angle section.

As mentioned hereinbefore, in many cases, the abdominal cavity is inflated with a pneumoperitoneum gas in order to prevent damages to intracavitary walls during an operation. In order to suppress leaks of the pneumoperitoneum gas in such a case, arrangements are usually made to minimize a dimensional difference between the inner diameter of the cannula 10 and the outer diameter of the endoscopic insertion instrument 3. Accordingly, the endoscopic insertion instrument 3 is tightly fitted in the cannula 10 in intimate contact with inner peripheral surfaces of the latter. This tight fitting and the existence of blade-like sharp edges at the fore end of the cannula 10 result in a problem that the outer skin layer of soft synthetic resin material in the angle section 3b of the insertion instrument 3 is readily scraped off when slid against the sharp fore edges of the cannula 10. Especially, in case the angle section 3b is in a bent state even in a slight degree when withdrawn into the cannula 10, it is very likely that the outer skin layer is scraped off to a conspicuous extent. In addition to considerable damages to the soft skin layer, the scraping involves another problem that debris of scraped skin layer remains in the body of the patient.

Figure 2:
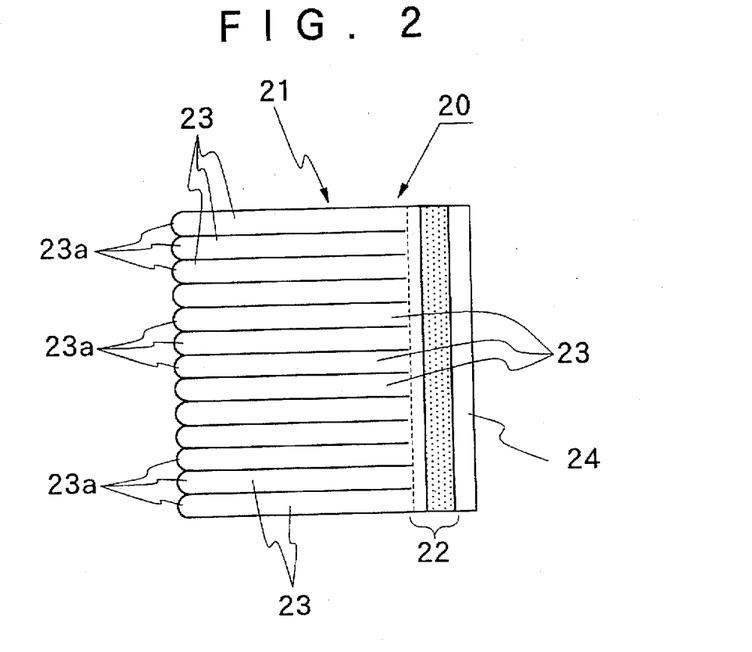
FIG. 2 is a schematic plan view of a protector girdle according to the present invention.
Figure 3:
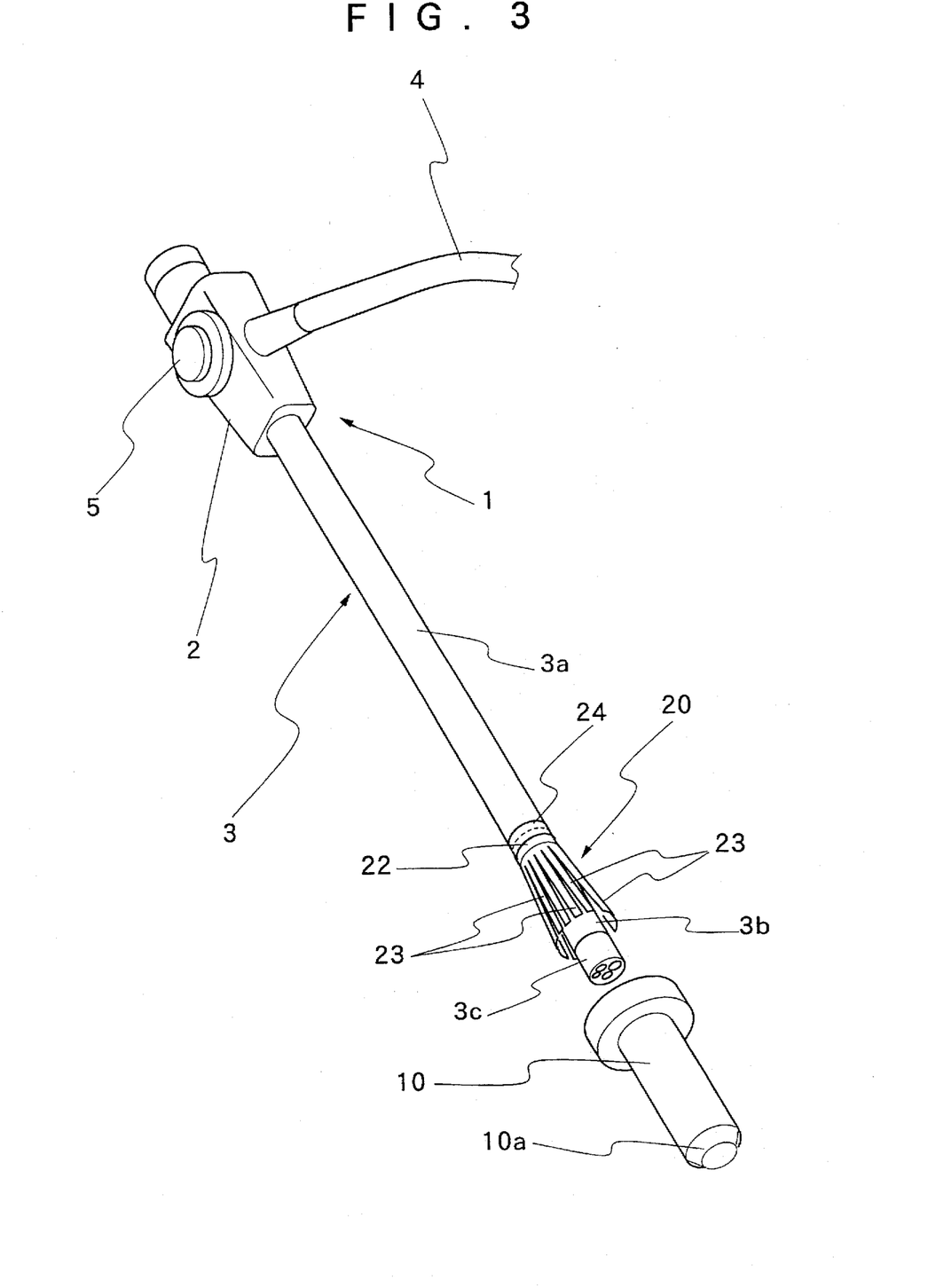
FIG. 3 schematically shows the protector girdle as fitted on an insertion instrument of an endoscope prior to introduction into a body cavity.
Figure 4:
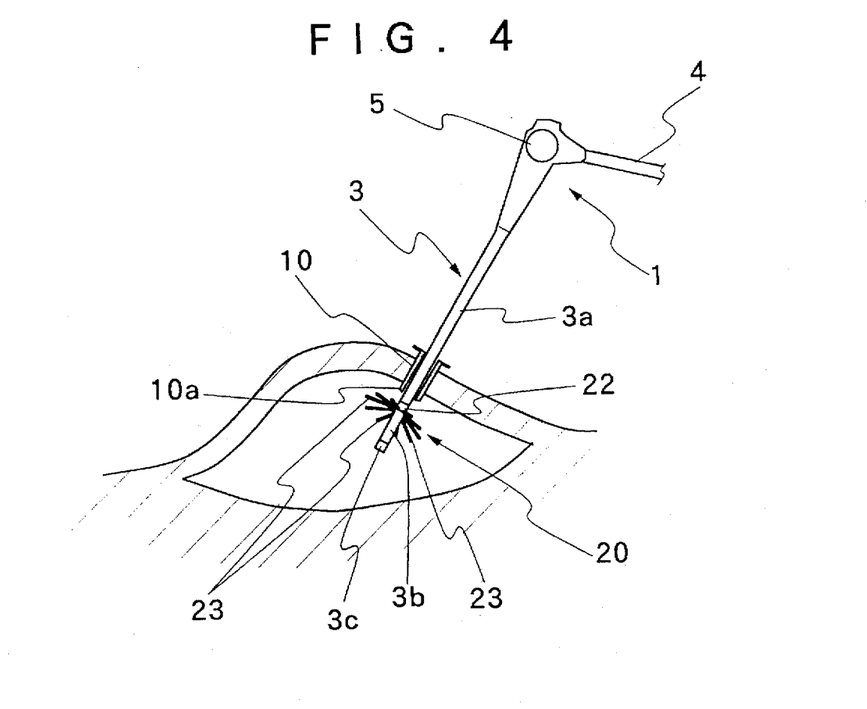
FIG. 4 is a schematic view of the endoscopic insertion instrument of FIG. 3 being introduced into a body cavity through a cannula of a trocar.

Referring to FIGS. 2 to 4, there is shown a protector girdle 20 according to the invention, which is to be fitted on the endoscopic insertion instrument 3 to protect the soft skin layer of the flexible angle section 3b from sharp edges at the fore end of the cannula 10. The protector girdle 20 consists of a generally rectangular sheet 21, preferably of a rigid polyethylene sheet with slippery surfaces and of a thickness of about several tens μm to impart suitable restorative stiffness. As shown in a developed view in FIG. 2, the girdle sheet 21 has at least a length corresponding to that of the angle section 3b, which normally has an axial length of approximately 8 cm to 10 cm, for covering the angle section completely when fitted on the insertion instrument 3. On the other hand, the girdle sheet 21 has a width which is equivalent to or slightly larger than a girth of an insertion instrument section around which the protector girdle is to be wrapped. Generally the endoscopic insertion instrument 3 has a diameter of about 10 mm and a girth of about 30 mm, so that normally the width along the longer side of the girdle sheet 21 measures about 30 mm or more.

The girdle sheet 21 essentially includes an adhesive band zone 22 and a plural number of flap cover strips 23. The adhesive band zone 22 is extended along one longer side of the girdle sheet 21 in a width of about 10 mm and provided with an adhesive layer on one side. The flap cover strips 23 are formed by slitting the remainder of the sheet in a predetermined pitch, e.g., in a pitch of 2 mm to 5 mm in the longitudinal direction of the adhesive band zone 22. Accordingly, a large number of flap cover strips 23 of the same width are formed perpendicularly on the front side of the adhesive band zone 22. The flap cover strips 23 are creased with a folding line as indicated by broken lines at the respective base ends which are connected to the adhesive band section 22, and are rounded off at corner edges of the respective fore free ends as indicated by reference numeral 23a.

Further, an adhesive anchor tape 24 is bonded on a non-adhesive outer side of the adhesive band zone 22. This anchor tape 24 has its adhesive face on the same side as the adhesive face of the band zone 22 and overlapped on the adhesive band zone 22 in an overhanging offset position, jutting out from proximal marginal edges of the adhesive band zone 22 by a predetermined width. A thin flexible tape, thinner by far than the girdle sheet 21, can be suitably used for the anchor tape 24 which is not required to have any restorative spring force or stiffness in particular.

In use of the protector girdle 20 with the above-described construction according to the invention, the girdle sheet 21 which constitutes a body structure of the protector girdle 20 can be fitted on the endoscopic insertion instrument 3 simply by bonding the adhesive face of the adhesive band 22 securely around boundary regions between the angle section 3b and the rigid section 3a while letting the flap cover strips 23 extend freely toward the distal end section 3c of the insertion instrument 3 in a forwardly diverging form. At this time, ideally the adhesive band zone 22 should be wrapped around the insertion instrument 3 such that its opposite end portions will meet in overlapped state. Although in some cases difficulties may be encountered in bonding the meeting ends of the band zone 22 in an overlapped state, it is desirable to butt the end portions without leaving any gap therebetween or to bond them in an overlapped state even in a slight degree. Along with and similarly to the adhesive band zone 22, the overhanging portions of the anchor tape 24 are also securely bonded around the insertion instrument 3. By so doing, the protector girdle 20 is securely anchored in position on the insertion instrument 3, covering the angle section 3b completely under the flap cover strips 23 which spread in a forwardly diverging form.

As seen in FIG. 3, the free ends of the flap cover strips 23 at the fore end of the protector girdle 20 somewhat tend to spread in radially outward direction in a free state, away from the insertion instrument 3. When introducing the endoscopic insertion instrument 3 into an abdominal cavity under guidance of a cannula 10 which percutaneously penetrates through abdominal walls as shown in FIG. 4, the protector girdle 20 is also introduced into the abdominal cavity in its entirety.

Figure 5:
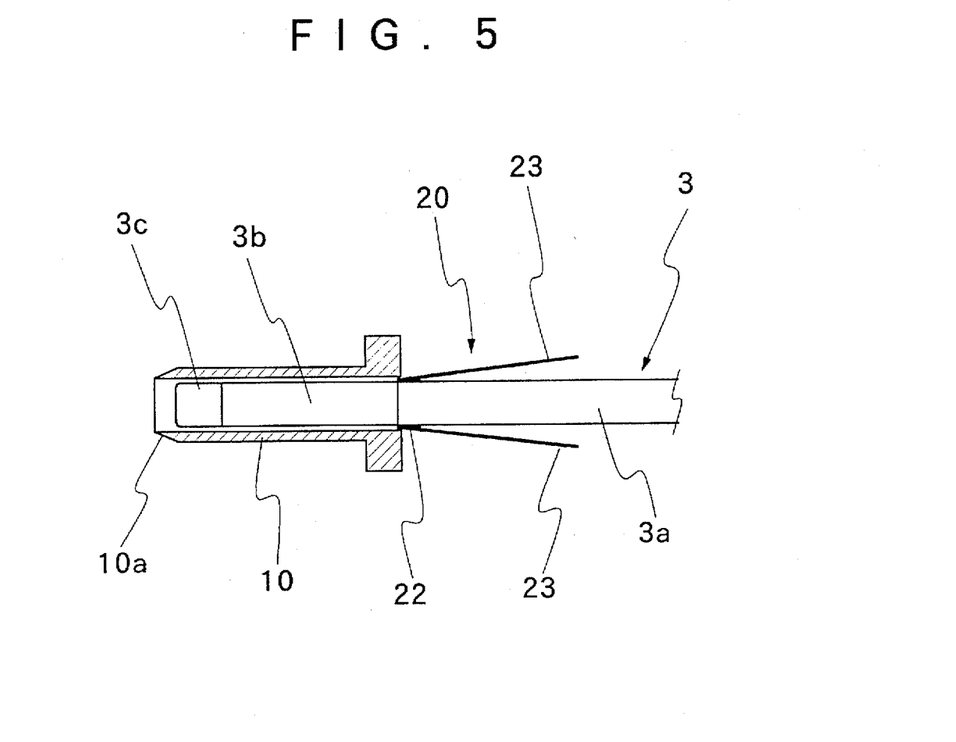
FIG. 5 is a schematic sectional view of the girdled endoscopic insertion instrument which has been inserted into the cannula up to a point where flap cover strips of the protector girdle folded back onto a proximal side of a flexible angle section of the insertion instrument.

More particularly, at a time point when the distal end section 3c of the endoscopic insertion instrument 3, which is fitted with the protector girdle 20 as shown in FIG. 3, is put into the cannula 10 for introduction into a body cavity, the respective flap cover strips 23 are in forwardly diverging positions, with widening spaces from both of the distal end portion 3c and angle section 3b in the forward direction. The flap cover strips 23 are folded back onto the proximal side of the angle section 3b at a point when their base end portions come into abutting engagement with the proximal end of the cannula 10. As soon as the proximal end of the cannula 10 reaches creased folding lines which bound the base ends of the flap cover strips 23 on the side of the adhesive band zone 22, the respective flap cover strips are folded back at the folding lines to lie flat on the insertion instrument 3. As the insertion instrument 3 is further introduced into the cannula 10, the angle section 3b comes into sliding contact with the sharp edges at the fore end of the cannula 10. However, as long as the insertion instrument 3 is in an inward or forward movement, there is no possibility of the outer skin layer of the angle section 3b being damaged by sliding contact with the sharp edges at the fore end of the cannula 10.

Figure 6:
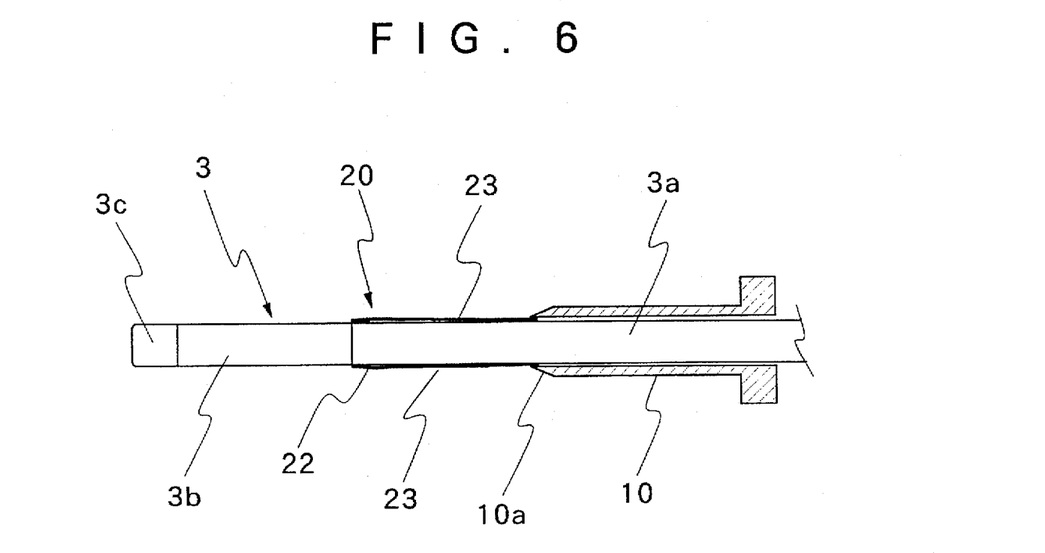
FIG. 6 is a schematic sectional view of the girdled endoscopic insertion instrument which has been inserted almost to a predetermined protruded position through the fore end of the cannula.

The flap cover strips 23 which have been folded back flat on the proximal side of the angle section 3b are now allowed to enter the cannula 10 from their folded ends, and to slip through the fore end of the cannula 10. As a result, the flap cover strips 23 are relieved of restraining actions of inner peripheral surfaces of the cannula 10 tend to return to original spread positions or forwardly diverging positions by resilient spring forces, away from the rigid section 3a of the insertion instrument 3. Therefore, even if the insertion instrument 3 is moved in a withdrawing direction, the free ends of the flap cover strips 23 are simply turned in the forward direction to some extent or just remain in free forwardly spread positions, without any possibility of being caught into the cannula 10.

The outer periphery of the angle section 3b is circumvented by the protector girdle 20, more specifically, by the flap cover strips 23 which are actually freely disposed in the forwardly spread positions as shown in FIG. 4, so that the angle section 3b can be operated free from restrictive interference by the flap cover strips 23 as it is bent in a certain direction as indicated by imaginary line in the same figure. Accordingly, in bending the angle section 3b by the angle knob 4 on the manipulating head 2 of the endoscope, no additional load is imposed on the angle knob 4 by the protector girdle 20.

Figure 7:
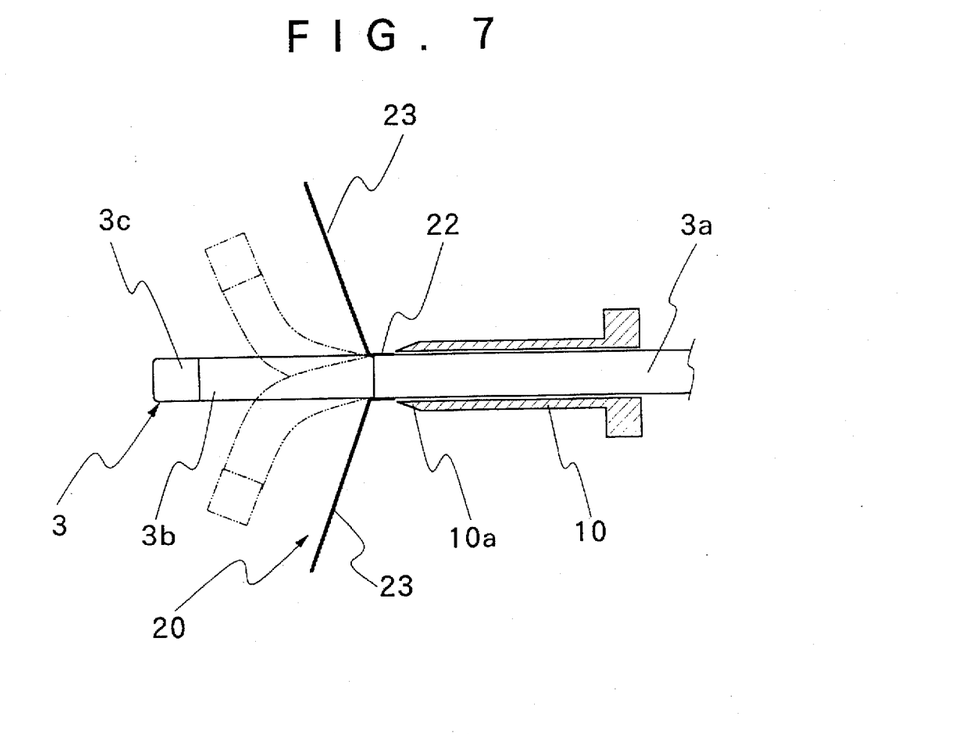
FIG. 7 is a schematic sectional view of the endoscopic insertion instrument being withdrawn into the cannula for extraction of the endoscope.
Figure 8:
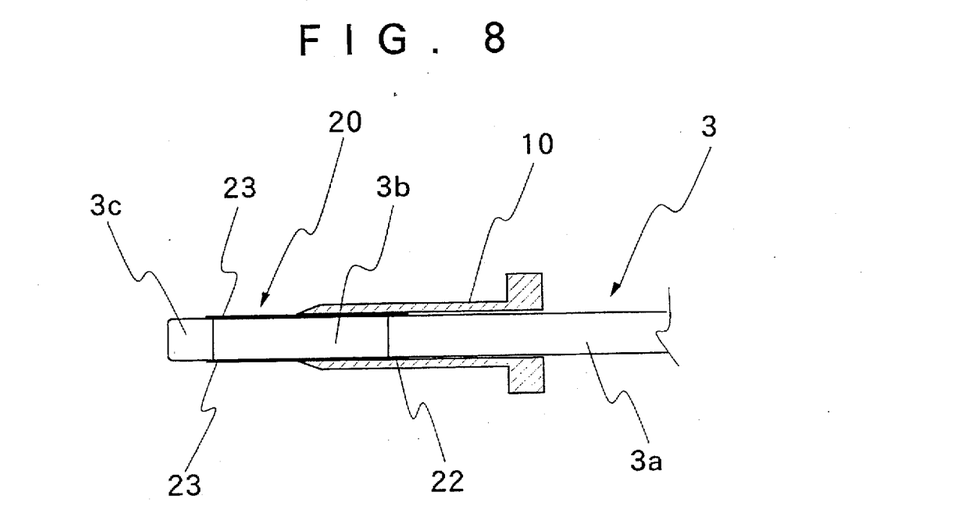
FIG. 8 is a schematic sectional view of the endoscopic insertion instrument which has been withdrawn into the cannula up to a halfway point of the angle section.

When withdrawing the insertion instrument 3 into the cannula 10 for extraction, the outer skin layer of the angle section 3b could be scraped off or damaged if contacted directly with sharp edges at the fore end 10a of the cannula 10 especially in case the angle section 3b is in a bent state even in a slightest degree as explained hereinbefore. In this regard, when the edges 10a of the cannula 10 are located on the proximal side of the angle section 3b, the flap cover strips 23 of the protector girdle 20 are allowed to spread apart away from the angle section 3b as shown in FIG. 7. Therefore, if the insertion instrument 3 is pulled outward to withdraw the angle section 3b into the cannula 10, the respective flap cover strips 23 are pushed and caused to lie flat on the angle section 3b by the fore edges 10a of the cannula 10. At this time, if the angle section 3b is in a bent state, the fore edges of the cannula 10 tend to bite on the flap cover strips 23. Even so, the flap cover strips, which are made of a rigid and slippery material and free at the respective fore ends, are simply pressed against the angle section 3b without sustaining any damages on their surfaces. Besides, by the pushing forces which are exerted on the flap cover strips 23 by the fore edges of the cannula 10, the flap cover strips 23 are resiliently pressed against the angle section 3b to correct same into a rectilinearly straightened state.

Figure 9:
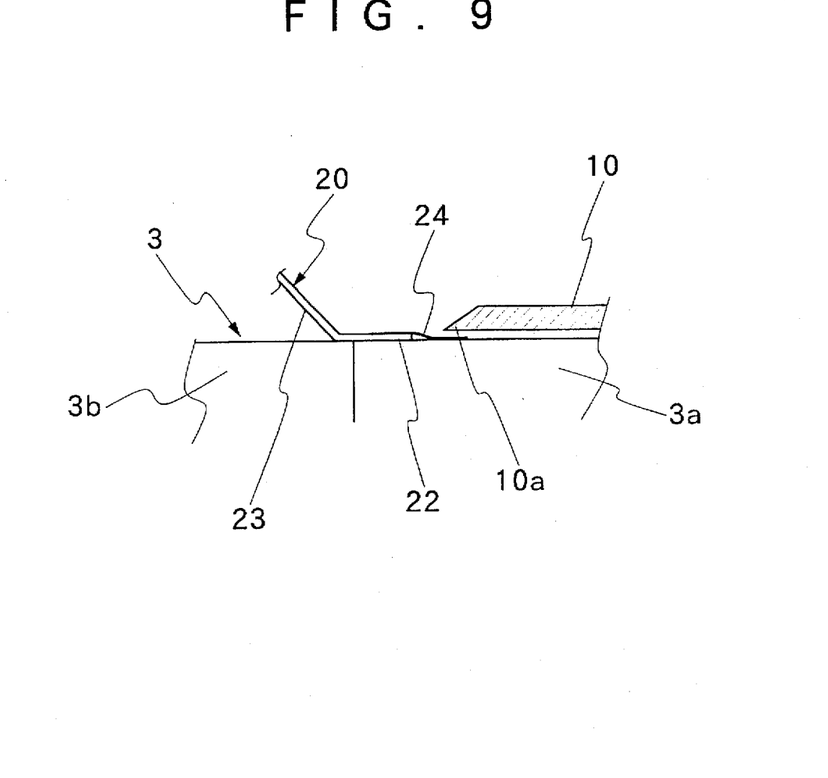
FIG. 9 is a schematic illustration explanatory of the manner in which sharp edges at the fore end of the cannula ride over the protector girdle on withdrawal of the endoscopic insertion instrument.

The boundary portions between the angle section 3b and the rigid section 3a, around which the adhesive band 22 of the protector girdle 20 is bonded, are necessarily passed through the fore edge 10a of the cannula 10 in order to protrude the distal end section 3c and angle section 3b of the endoscopic insertion instrument 3 completely out of the cannula 10. Therefore, at the time of extraction of the insertion instrument 3, it becomes necessary to let the fore edges 10a of the cannula 10 smoothly ride onto proximal end portions of the adhesive band zone 22 of the protector girdle 20. Otherwise, the fore edges of the cannula 10 could get caught on the proximal end of the adhesive band zone 22 if the latter is exposed on the insertion instrument 3 in a stepped form. However, this problem is eliminated by the adhesive anchor tape 24 which wrapped on the proximal end of the band zone 22. As shown in FIG. 9, the adhesive anchor tape 24 is extremely thin and therefore can let the fore edges 10 of the cannula 10 smoothly ride onto the adhesive band zone 22 in the course of withdrawal of the insertion instrument.

Figure 10:
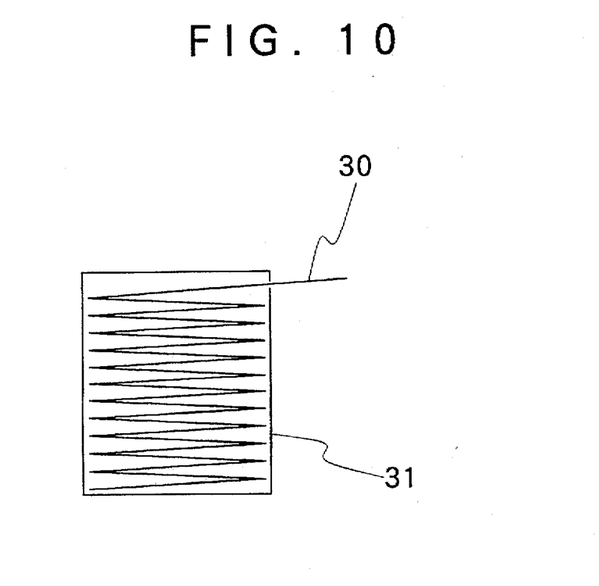
FIG. 10 is a schematic illustration of a stock box for the protector girdles.
Figure 11:
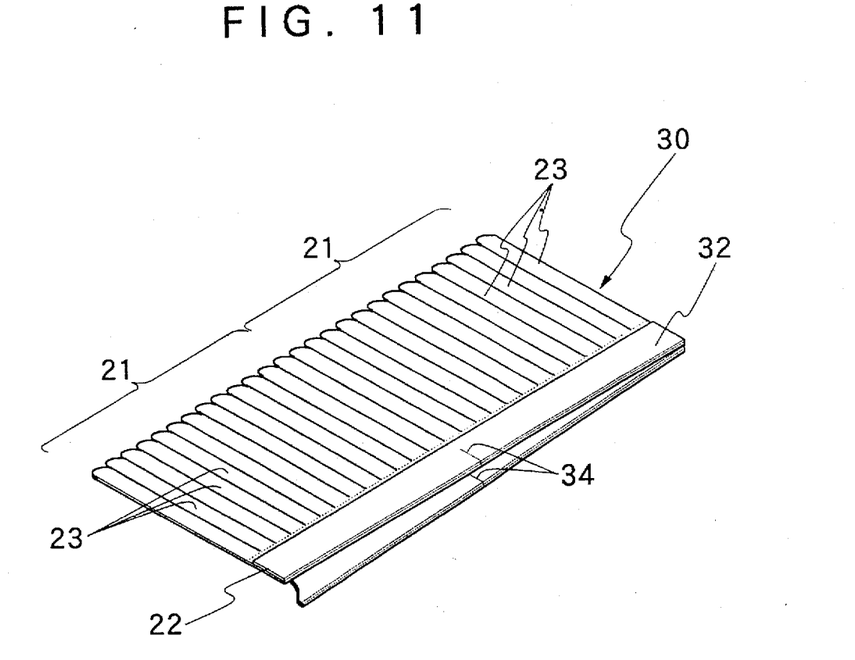
FIG. 11 is a schematic perspective view of a continuous girdle sheet which is alternately folded for storage in the stock box.

From the standpoint of preventing secondary infections, a used protector girdle should preferably be removed and disposed of in a suitable manner. In order to keep a stock of protector girdles, it would be advantageous to keep a continuous protector girdle sheet, which contains a large number of protector girdle units in a continuously connected form. A continuous girdle sheet of this sort can be put in a stock box in an alternately folded form as shown in FIG. 10 and cut into a suitable unit length depending upon the size of an endoscopic insertion instrument 3 to be girdled. In such a case, a separator sheet 32 is bonded on the adhesive faces of the band zone 22 and anchor tape 22 to keep same in an unexposed state while in storage. In order to make the continuous girdle sheet easily dividable into individual units without using scissors or other cutting jigs, short slits may be provided across the adhesive band zone 22 at predetermined intervals or at a number of different positions depending upon girth sizes of endoscopic insertion instruments. Alternatively, cut lines for insertion rod of particular size or sizes may be marked at intervals along the length of the continuous sheet.

What is claimed is:

1. A protector girdle to be wrapped around an endoscopic insertion instrument prior to introduction into a body cavity through a cannula of a trocar for protecting a soft skin layer on a flexible section of the insertion instrument from sharp edges at the fore end of the cannula, said protector girdle comprising:

a generally rectangular sheet of rigid and slippery material with a restorative spring force;

an adhesive band zone defined in a predetermined width along one side of said rectangular sheet; and a large number of elongated flap cover strips cut in the remainder of said sheet in a predetermined pitch along said adhesive band zone and having free ends on the other side of said sheet material remote from said adhesive band zone;

said protector girdle being fitted on the endoscopic insertion instrument by bonding said adhesive band around a proximal end portion of the flexible section of the insertion instrument in such a manner as to cover the soft skin layer under said flap cover strips.

2. A protector girdle as defined in claim 1, wherein said flap cover strips are rounded off at corner edges of said free ends.

3. A protector girdle as defined in claim 1, further comprising an adhesive anchor tape bonded on the endoscopic insertion instrument in such a way as to wrap in proximal end portions of said adhesive band zone.

4. A protector girdle as defined in claim 1, wherein said flap cover strips are each creased with a folding line at a base end connected to said adhesive band zone.

5. A protective girdle as defined in claim 1, wherein said protector girdle is provided in the form of a continuous girdle sheet containing a large number of continuously connected protector girdle units each containing said adhesive band zone and a large number of said flap cover strips.

6. A protector girdle as defined in claim 5, further comprising a separator sheet bonded on adhesive band zones of the respective protector girdle units on said continuous girdle sheet.

7. A protector girdle as defined in claim 5, wherein said continuous girdle sheet is provided with slits at predetermined cut positions for dividing said continuous sheet into unit lengths corresponding to a girth size of an endoscopic insertion instrument.

8. A protector girdle as defined in claim 7, wherein said continuous girdle sheet is put in a container box in an alternately folded state.

* * * * *